United States Patent [19]

Pistorius

[11] Patent Number: 4,557,873

[45] Date of Patent: Dec. 10, 1985

[54] PROCESS FOR ISOLATING PARAFFINSULFONATES AND SULFURIC ACID OF LOW ALKALI METAL SULFATE CONTENT FROM PARAFINSULFOXIDATION REACTION MIXTURES

[75] Inventor: Rudolf Pistorius, Hünstetten, Fed. Rep. of Germany

[73] Assignee: Hoechst Aktiengesellschaft, Fed. Rep. of Germany

[21] Appl. No.: 674,581

[22] Filed: Nov. 26, 1984

[30] Foreign Application Priority Data

Nov. 28, 1983 [DE] Fed. Rep. of Germany ....... 3342984

[51] Int. Cl.$^4$ .......................................... C07C 143/02
[52] U.S. Cl. .......................... 260/513 R; 260/504 S; 260/504 R
[58] Field of Search ............. 260/513 R, 504 S, 504 R

[56] References Cited

U.S. PATENT DOCUMENTS

| | | | |
|---|---|---|---|
| 3,454,479 | 7/1969 | Hopkins et al. | 260/513 R |
| 3,481,849 | 12/1969 | Beermann et al. | 260/513 R |
| 3,577,456 | 5/1971 | Kleiner et al. | 260/513 R |
| 3,988,218 | 10/1976 | Susuki et al. | 260/513 R |
| 4,054,599 | 10/1977 | Shuttleworth | 260/513 R |
| 4,177,208 | 12/1979 | Boy et al. | 260/513 R |
| 4,454,075 | 6/1984 | Mees et al. | 260/513 R |

Primary Examiner—Alan Siegel
Attorney, Agent, or Firm—Connolly and Hutz

[57] ABSTRACT

Process for isolating paraffinsulfonates and sulfuric acid of low alkali metal sulfate content from paraffinsulfoxidation reaction mixtures with the aid of alcohols, which comprises adding a $C_4$–$C_8$-alcohol to the reaction mixture, which has been freed from sulfur dioxide, removing the lower phase of dilute sulfuric acid which separates out, adding to the remaining upper product phase (1) an amount of alkali metal hydroxide such that two phases form and bringing the upper product phase (2) thus obtained to a pH value of 9–12 by addition of some of the product phase (1) and concentrating it by evaporation. For better utilization of the alkali during neutralization, this step can also be carried out in three stages. Only an alkali metal sulfate solution is then obtained as the waste product.

2 Claims, 1 Drawing Figure

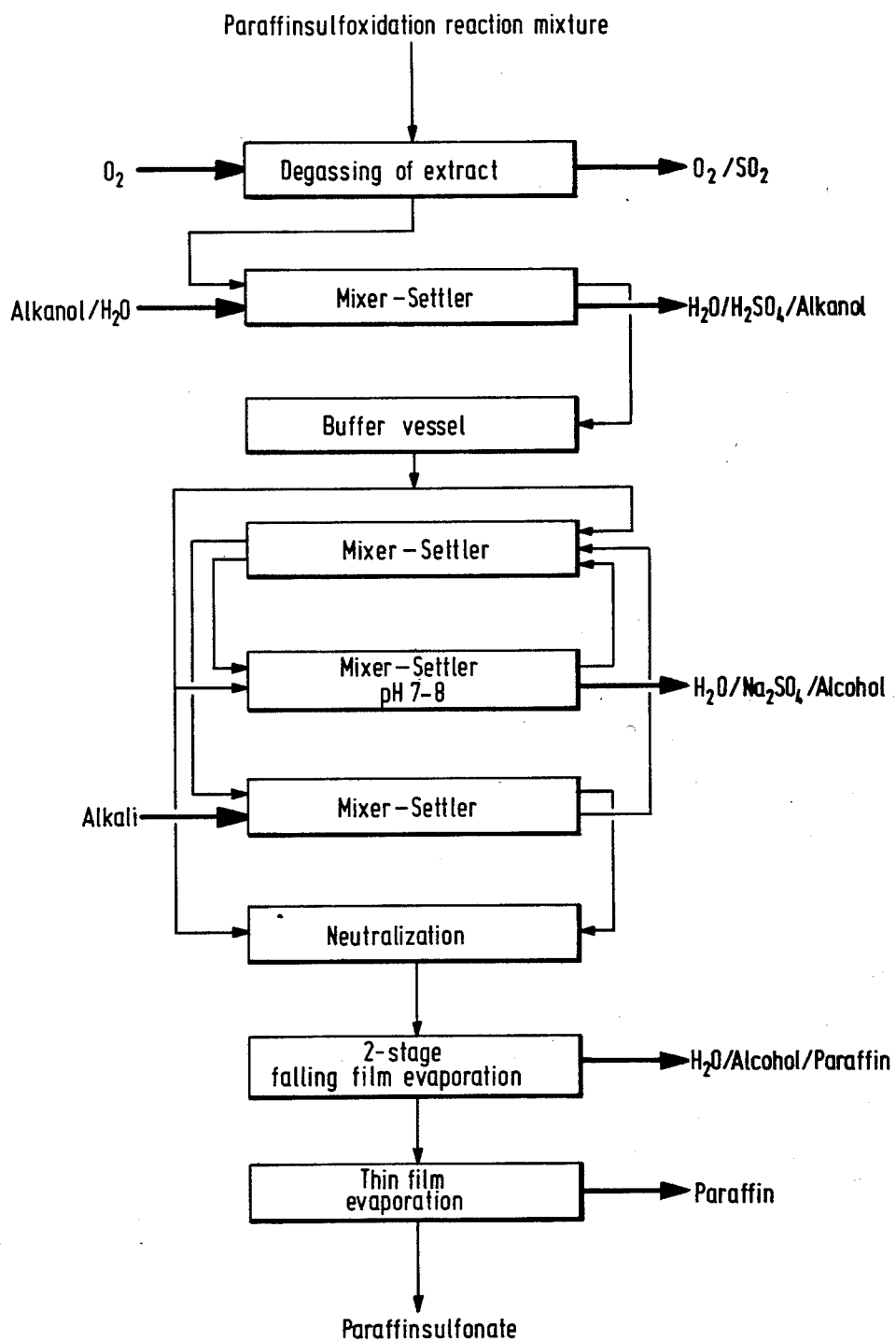

PROCESS FOR ISOLATING PARAFFINSULFONATES AND SULFURIC ACID OF LOW ALKALI METAL SULFATE CONTENT FROM PARAFINSULFOXIDATION REACTION MIXTURES

The aqueous solutions of paraffinsulfonic acids obtainable by sulfoxidation of n-paraffins, for example by the process in German Pat. No. 910,165, also additionally contain sulfur dioxide, sulfuric acid and hydrotropically dissolved paraffins. In order to isolate useful paraffinsulfonic acids or paraffinsulfonates of high quality from such reaction mixtures, i.e. light-colored, substantially odorless products with the lowest possible sulfuric acid or salt content, sulfur dioxide, sulfuric acid and paraffins must be removed as quantitatively and as gently as possible. The paraffinsulfoxidation products already start to decompose at temperatures above 50° C., which manifests itself externally by discoloration of the acid reaction mixture from water-clear via yellowish and brown to, finally, deep black. Although the amount of paraffinsulfonic acid decomposed by the action of heat is still relatively low as long as the acid reaction mixtures are not exposed to temperatures above 100° C. for a prolonged period, because of their color intensity even a small amount of decomposed products necessitates a considerable consumption of bleach if perfectly light-colored products are to be obtained.

It has been found that, in contrast, alkaline salts of paraffinsulfonic acids are relatively stable. Temperatures below 200° C. lead to only quite insigificant discolorations, even over a prolonged period of heating, and even higher temperatures up to about 260° C. result in discoloration which can still easily be removed again with small amounts of bleaching agent.

Care must therefore already be taken in the first step of the working up of the paraffinsulfoxidation reaction mixtures, i.e. during degassing to remove the sulfur dioxide, that as far as possible no discoloration occurs. If the degassing is carried out under a weak vacuum, only very brief warming to about 85° C. is required to achieve almost complete removal of the sulfur dioxide. Bubbling out with inert gas or with pure oxygen in a column filled with a suitable packing at a temperature of about 40°–70° C. is also possible.

By immediate subsequent recooling of the reaction mixture to room temperature, noticeable decomposition, i.e. the start of a deepening in the color of the reaction mixture, can be prevented in this process step.

In view of the quality of the paraffinsulfonate, it would be advisable to neutralize the reaction mixture immediately after the degassing. However, because of the high consumption of alkali required to neutralize the sulfuric acid and because of the considerable losses of paraffinsulfonate which occur during removal of the alkali metal sulfate by filtration, such a procedure is uneconomical and requires technical effort.

After the sulfur dioxide has been removed from the reaction mixture, attempts must therefore be made to remove as much of the sulfuric acid as possible from the mixture before the neutralization, whilst protecting the paraffinsulfonic acid. In the known processes which attempt to achieve such an aim, a procedure is in general followed in which the degassed sulfoxidation mixture is treated with a suitable organic solvent to cause demixing into an organic phase, which contains the paraffinsulfonic acids, and an aqueous phase, which contains the sulfuric acid as far as possible in the form of a generally 10 to 25% strength aqueous solution. The two phases are then separated and the organic phase is further worked up for isolation of the paraffinsulfonic acids or their salts. Thus, it is already known from German Patent Application No. F 3,718,120, published on 29.1.1953, that organic solvents which are water-insoluble or have only a limited water-miscibility, such as, for example, benzene, chlorobenzene, cyclohexane, carbon tetrachloride, chloroform, methylene chloride and the like, can be added to the sulfoxidation mixture to remove the sulfuric acid. According to German Offenlegungsschrift No. 2,730,245, ethers, such as, for example, diethyl ether or di-n-butyl ether, are also used for the same purpose, and according to German Offenlegungsschrift No. 2,745,691, ketones or esters are also used, and according to German Offenlegungsschrift No. 2,139,477, alcohols with at least 5 carbon atoms are also used.

None of these known processes for removing sulfuric acid at low temperatures have yet found acceptance on a large industrial scale, because either the expenditure on distillative working up of the product solution was too high and/or the degree of separation of the sulfuric acid from the reaction mixture was insufficient finally to obtain products with a low salt content of less than 2% by weight of residual salt (based on 100% of paraffinsulfonate).

Thus, for example, with alcohols with 4 to 6 carbon atoms, removal of the sulfuric acid by single-stage extraction is only so incomplete that the salt content in the neutralized end product is still substantially above 2% by weight (based on the paraffinsulfonate), even if the amount of alcohol added is increased to 30% by weight (based on the degassed sulfoxidation reaction mixture). On the other hand, larger or smaller amounts of alcohol lead to even less complete separating out of the sulfuric acid.

However, if, for example, water is also added after separating out with hexanol, in order to wash further sulfuric acid out of the reaction mixture (2-stage extraction) so that the final residual salt content in the paraffinsulfonate does not exceed 2% by weight (again based on the detergent substance), it is found that not inconsiderable amounts of water are required for this, and only a smaller proportion of these are separated out again, which means that there is a very great increase in the expenditure on distillation.

On the one hand, the degree of separation of the sulfuric acid increases as the number of carbon atoms in the alcohols employed increases, but on the other hand the expenditure on working up increases as the boiling points of the alcohols used increase.

The invention relates to a process for isolating paraffinsulfonates and sulfuric acid of low alkali metal sulfate content from paraffinsulfoxidation reaction mixtures with the aid of alcohols, which comprises adding a $C_4$–$C_8$-alcohol to the reaction mixture, which has been freed from sulfur dioxide, removing the lower phase of dilute sulfuric acid which separates out, adding to the remaining upper product phase (1) an amount of alkali metal hydroxide such that two phases form and bringing the upper product phase (2) thus obtained to a pH value of 9–12 by addition of some of the product phase (1) and concentrating it by evaporation.

The starting point is the reaction mixture which is obtained on sulfoxidation of n-paraffins, in particular $C_{13}$–$C_{18}$-paraffins, and which has been freed from sulfur dioxide by degassing, this mixture being stirred with 15 to 30% by weight, in particular 17 to 25% by weight, of a $C_4$–$C_8$-alcohol at temperatures of 15° to 80° C., in particular at 25° to 35° C. Isobutanol is preferred here.

After 5 to 35 minutes, in general already after about 15 minutes, such a mixture separates into 2 phases, the lower phase of which, which contains about 15–20% strength aqueous sulfuric acid with about 0.1 to 3% by weight of the alcohol, is removed.

45–55% strength, in general 50% strength, potassium or sodium hydroxide solution is added to most (about 60 to 75%) of the upper phase, containing paraffinsulfonic acid/alcohol, in an amount such that, at 80°–90°, a lower phase containing some of the excess base and most of the residual sulfuric acid in the form of alkali metal sulfate separates out. The paraffinsulfonate solution which has thus been substantially freed from the residual salt but still contains excess alkali is brought to a pH value of about 9 to 12, in general 11 (measured with a glass electrode) by addition of the remaining 25–40% of the paraffinsulfonic acid/alcohol phase. The solution thus obtained is then evaporated to a melt in a thin film evaporator in vacuo, in countercurrent.

In the procedure thus described, an aqueous alkali metal sulfate/alkali solution would be obtained, leading to an undesirably high consumption of alkali. However, if the treatment with excess alkali is carried out in 3 stages, as described below, the alkali is utilized completely for the neutralization and only an aqueous sodium sulfate solution is obtained, from which, if necessary, the sulfate can easily be precipitated as gypsum by addition of, for example, $CaCl_2$ and hence can be removed.

The starting product here is again the degassed paraffinsulfoxidation reaction mixture or the paraffinsulfonic acid/alcohol phase, as described above, obtained after addition of the alcohol. This solution is introduced continuously into an apparatus consisting of three combined mixing/settling vessels (so-called mixer-settlers) and another mixing vessel. The dimensions of the mixer-settlers are such that a residence time of about 10 to 20 minutes is established in the particular settler part. All 3 mixer-settlers are operated at 80°–90° C.

The paraffinsulfonic acid/alcohol solution, the upper phase of the 2nd settler and the lower phase of the 3rd settler are metered into the 1st mixer and the lower phase of the 1st settler and an amount of the paraffinsulfonic acid/alcohol solution such that the pH value in the 2nd mixer-settler is always between 7 and 8 are metered into the 2nd mixer. The 3rd mixer accommodates the total amount of alkali metal hydroxide solution required, and the product phase of the 1st settler. The lower phase, which consists of an aqueous alkali metal sulfate solution with a trace of alcohol (less than 1% by weight), is discharged from the 2nd settler and the upper phase, which is brought to a pH value of about 11 in the mixing vessel with further paraffinsulfonic acid/alcohol solution, is discharged from the 3rd settler. This solution is then evaporated to the desired degree of concentration. The flow chart of this variant of the process claimed is shown in the drawing. Both variants have the common essential characteristic that substantial removal of the sulfuric acid or of the sulfate is achieved by renewed formation of two phases as a result of the addition of excess alkali metal hydroxide.

A substantial advantage of the process according to the invention is that it is possible to obtain light-colored products with little odor in a very economical manner, which is chiefly effected by separating out the predominant proportion of sulfuric acid under exceptionally mild conditions. By the procedure described above in the neutralization of the paraffinsulfonic acid to paraffin-sulfonates, it is possible at the same time to obtain products with an extremely low salt content by discharging further aqueous sodium sulfate.

EXAMPLE 1

A sulfoxidation reaction mixture composed of 41.0% of $H_2O$, 7.13 of $H_2SO_4$, 20.38% of $RSO_3H$ and 31.49% of paraffin is used. The paraffin used here and in the following examples is a mixture of $C_{13}$–$C_{17}$-paraffins. R accordingly denotes a mixture of $C_{13}$ to $C_{17}$-alkyl.

200 g of hexanol saturated with water are added to 1,000 g of the reaction mixture at room temperature, 369.2 g of dilute aqueous sulfuric acid separating out as a lower phase.

The upper phase (paraffinsulfonic acid/hexanol solution) then contains 0.73% of sulfuric acid and 24.86% of paraffinsulfonic acid.

400 g of this phase are stirred with 64 g of 50% strength sodium hydroxide solution at 80° C. for 5 minutes.

After a settling time of 15 minutes, 52 g separates out as an aqueous lower phase containing 4.5% of $Na_2SO_4$ and 18% of NaOH. The upper product phase is brought to a pH value of 11 with 119 g of the paraffin-sulfonic acid/hexanol solution and is evaporated in a thin film evaporator under 30 mm Hg at a heating oil temperature of 230° C. to a melt, which has the following composition: 97.6% of $RSO_3Na$, 0.8% of paraffin and 1.6% of $Na_2SO_4$.

EXAMPLE 2

1,000 g of the same sulfoxidation reaction mixture as in Example 1 are stirred with 200 g of isobutanol and 34 g of water at 28° C. for 2 minutes and the mixture is left to stand for 3 hours.

The upper phase then contains 0.87% of sulfuric acid and 24.01% of paraffinsulfonic acid. 400 g of this phase are stirred with 68 g of 50% strength sodium hydroxide solution for 3 minutes and the mixture is left to stand at 85°–88° C. for 15 minutes. 69 g of aqueous phase containing 17.6% of sodium hydroxide solution and 6.1% of sodium sulfate separate out. The upper phase is then brought to pH 11 with 114 g of paraffinsulfonic acid/isobutanol solution, and is then evaporated under 30 mm Hg in a thin film evaporator (heating oil temperature of 230° C.). The resulting melt has the following composition: 97.4% of $RSO_3Na$, 0.8% of paraffin and 1.8% of $Na_2SO_4$.

EXAMPLE 3

2,060 g of isobutanol, 500 g of $H_2O$ and 50 g of paraffin are added to 10.28 kg of reaction mixture composed of 4,240 g of $H_2O$, 2,160 g of $RSO_3H$, 740 g of $H_2SO_4$ and 3,140 g of paraffin. After one hour, 4,020 g of a lower phase containing 3,240 g of water, 660 g of sulfuric acid and 120 g of isobutanol were removed. The upper phase (8,870 g), which has a low sulfuric acid content, consists of 1,500 g of $H_2O$, 2,160 g of paraffinsulfonic acid, 80 g of sulfuric acid, 3,190 g of paraffin and 1,940 g of isobutanol. 500 g per hour of this phase were metered continuously into the 1st mixer of an apparatus consisting of 3 mixer-settlers operated at 85°–90° C. and a downstream mixing apparatus, the upper phase of the 2nd settler (about 234 g/hour) and the lower phase of the 3rd settler (about 195 g/hour) flowing into the 1st mixer at the same time. 84 g of 50% strength sodium hydroxide solution and the upper phase of the 1st settler (about 800 g/hour) are at the same time metered into the 3rd mixer, whilst about 689 g/hour (composition: 123 g of $H_2O$, 173 g of $RSO_3H$, 1 g of $Na_2SO_4$, 238 g of paraffin, 143 g of isobutanol and 11 g of NaOH) of the upper phase of the 3rd settler flow into the mixing apparatus, and are brought to a pH value of about 11 with 228 g/hour of upper phase of low sulfuric acid content (composition: 39 g of $H_2O$, 56 g of $RSO_3H$, 2 g of $H_2SO_4$, 81 g of paraffin and 50 g of isobutanol). An isobutanol/paraffin/paraffinsulfonate solution of the following composition results: 168 g of $H_2O$, 233 g of $RSO_3Na$, 4 g of $Na_2SO_4$, 319 g of paraffin and 192 g of isobutanol (917 g/hour), this mixture being evaporated on a thin film evaporator under 30 mm Hg (heating fluid temperature 230° C.). 236 g of paraffinsulfonate, which still contain 4 g of $Na_2SO_4$ and 2 g of paraffin, result.

The upper phase of the 1st settler (about 129 g/hour) flows into the 2nd mixer and is mixed with an amount of upper phase of low sulfuric acid content (about 159 g/hour - composition: 26 g of $H_2O$, 31 g of $RSO_3H$, 1 g of $H_2SO_4$, 59 g of paraffin and 35 g of isobutanol) such that a pH value of 7–8 is established. The lower phase of the 2nd settler consists of aqueous sodium sulfate solution (54 g/hour) (composition: 45 g of $H_2O$, 8 g of $Na_2SO_4$ and 1 g of isobutanol), which is discharged.

I claim:

1. A process for isolating paraffinsulfonates and sulfuric acid of low alkali metal sulfate content from paraffinsulfoxidation reaction mixtures with the aid of alcohols, which comprises adding a $C_4$–$C_8$-alcohol to the reaction mixture, which has been freed from sulfur dioxide, removing the lower phase of dilute sulfuric acid which separates out, adding to the remaining upper product phase (1) an amount of alkali metal hydroxide such that two phases form and bringing the upper product phase (2) thus obtained to a pH value of 9–12 by addition of some of the product phase (1) and concentrating it by evaporation.

2. The process as claimed in claim 1, wherein the upper product phase (1) which remains is introduced into a settling vessel (1), together with the lower phase from a settling vessel (3) and the upper phase from a settling vessel (2), the upper phase obtained in the settling vessel (1) is introduced into the settling vessel (3), together with an amount of alkali metal hydroxide such that two phases form, the lower phase obtained in settling vessel (1) is introduced into a settling vessel (2) at the same time as an amount of product phase (1) such that a pH value of 7 to 8 is maintained, the upper phase obtained in the settling vessel (2) is introduced into the settling vessel (1), the lower phase obtained in the settling vessel (2), consisting essentially of a water/$Na_2SO_4$/$C_4$–$C_8$-alkanol mixture, is removed from the process, the lower phase obtained in the settling vessel (3) is introduced into the settling vessel (1), together with the product phase (1), and the lower phase obtained in settling vessel (3) is brought to a pH value of 9–12 by addition of part of the product phase (1) and is concentrated by evaporation.

* * * * *